(12) United States Patent
Calasso et al.

(10) Patent No.: US 11,752,256 B2
(45) Date of Patent: Sep. 12, 2023

(54) MEDICAL INFUSION DEVICE

(71) Applicant: Medirio S.A., Visp (CH)

(72) Inventors: Irio Giuseppe Calasso, Visp (CH); Matteo De Donatis, Visp (CH)

(73) Assignee: Medirio S.A., Visp (CH)

( * ) Notice: Subject to any disclaimer, the term of this patent is extended or adjusted under 35 U.S.C. 154(b) by 78 days.

(21) Appl. No.: 17/576,532

(22) Filed: Jan. 14, 2022

(65) Prior Publication Data

US 2022/0133985 A1 May 5, 2022

Related U.S. Application Data

(62) Division of application No. 16/142,887, filed on Sep. 26, 2018, now abandoned.

(30) Foreign Application Priority Data

Sep. 27, 2017 (IT) .......................... 102017000108005

(51) Int. Cl.
*A61M 5/14* (2006.01)
*A61M 5/142* (2006.01)
*A61M 5/168* (2006.01)

(52) U.S. Cl.
CPC ........ *A61M 5/14228* (2013.01); *A61M 5/142* (2013.01); *A61M 5/1413* (2013.01); *A61M 5/14212* (2013.01); *A61M 5/14248* (2013.01); *A61M 5/14276* (2013.01); *A61M 5/16813* (2013.01); *A61M 2005/14208* (2013.01); *A61M 2005/14268* (2013.01); *A61M 2205/103* (2013.01); *A61M 2205/3365* (2013.01); *A61M 2205/3515* (2013.01); *A61M 2205/3569* (2013.01); *A61M 2205/8206* (2013.01); *A61M 2205/8237* (2013.01); *A61M 2205/8243* (2013.01); *A61M 2205/8287* (2013.01)

(58) Field of Classification Search
CPC ............ A61M 5/14228; A61M 5/1413; A61M 5/142; A61M 5/14248
See application file for complete search history.

(56) References Cited

U.S. PATENT DOCUMENTS

| | | |
|---|---|---|
| 10,105,080 B1 | 10/2018 | Kam |
| 2007/0270744 A1 | 11/2007 | Dacquay |
| 2010/0130932 A1 | 5/2010 | Yodfat |
| 2011/0196337 A1 | 8/2011 | Brandt |

(Continued)

FOREIGN PATENT DOCUMENTS

| | | |
|---|---|---|
| EP | 1 272 092 B1 | 5/2005 |
| EP | 2 022 518 A1 | 2/2009 |

(Continued)

*Primary Examiner* — Courtney B Fredrickson
(74) *Attorney, Agent, or Firm* — BLANK ROME LLP

(57) ABSTRACT

An infusion system for infusing a medication in a patient, comprising a medication dose dispensing device and a control device for controlling the dispensing device. The infusion system can be configured in a non-operating configuration, in which the dispensing device and the control device are spaced apart from each other, and in an operating configuration, in which the dispensing device and the control device are temporarily proximity-coupled. The actuating rotor of the control device and the actuated rotor of the dispensing device have a common rotation axes, and the system can compensate or block the rotation of the control device with respect to the dispensing device.

15 Claims, 6 Drawing Sheets

(56) References Cited

U.S. PATENT DOCUMENTS

| | | |
|---|---|---|
| 2012/0203177 A1 | 8/2012 | Lanier, Jr. et al. |
| 2016/0235913 A1 | 8/2016 | Smith |

FOREIGN PATENT DOCUMENTS

| | | |
|---|---|---|
| EP | 2 617 445 B1 | 7/2013 |
| EP | 2 764 881 B1 | 8/2014 |
| EP | 2 910 263 A1 | 8/2015 |
| EP | 2 379 132 B1 | 9/2016 |
| EP | 3 138 592 A1 | 3/2017 |
| EP | 3 138 594 A1 | 3/2017 |
| WO | WO 2010/07201 | 7/2010 |

MEDICAL INFUSION DEVICE

This is a divisional of U.S. application Ser. No. 16/142,887, filed Sep. 26, 2018, which claims priority to Italy Application No. 102017000108005, filed Sep. 27, 2017, the disclosures of which are herein incorporated by reference.

FIELD OF THE INVENTION

The present invention relates to a device for infusing a medication in a patient, in particular for trans-dermal or subcutaneous infusion.

BACKGROUND ART

Several diseases require regular infusion of medication doses over a prolonged period of time or for chronic therapy. In many cases, these medications are in the form of solutions for a trans-dermal infusion. A typical example is diabetic patients, who require several infusions of insulin every day, or patients suffering from painful pathologies, very often chronic, who need the regular intake of painkillers.

In addition to traditional syringes or infusion pens (for example, the insulin pen), infusion devices are also used having a subcutaneously implanted needle connected to the dose dispensing device of the medicine. These latter devices are installed on the patient's body, so that the dose of the medicine can be released on a regular basis or on specific needs.

In order to make these tools as simple as possible to be used, light, safe and cost-effective, the current Applicant has developed innovative devices, protected by various patent/patent applications.

EP 2379132 B1 discloses a transdermal infusion system comprising:
- a device for dispensing a medication to a patient, placed in contact with the patient's skin, provided with a medication tank, an element for transdermal injection and a control unit to monitor and control the dispensing of the medication, wherein the control unit comprises i) one or more rotors and one or more pumping means and ii) at least one safety lock mechanism of the dispensing when not required,
- a separate control device, adapted to transfer the energy necessary for the dispensing of a dose and to release the safety locking mechanism only when the actuation device is placed near the release device.

EP 2617445 B1 discloses an infusion system as defined above, comprising a position sensor for detecting if the dispensing device and the control device are in the proximity operative position and a controller for controlling the dispensing of the dose only if the correct position is detected.

EP 1272092 B1 discloses a system similar to that of EP 2379132 B1, wherein the system provides a pre-operating condition in which the system is in non-operational condition and an operating condition in which the system is operational.

EP 2764881 B1 discloses a system similar to that of EP 2379132 B1, comprising an electronic control system for the correct operation of the system, wherein the medication dispensing device comprises a transponder, while the control device comprises a device for the transmission/reception of signals and controls.

EP 3138592 A1 and EP 3138594 A1 disclose a system similar to that of EP 2379132 B1, comprising a system for blocking the operation of the medication dispensing device in the event of a malfunction.

EP 2910263 A1 discloses a rotor locking/unlocking system of a medication dispensing device as defined above, comprising a magnetic release system.

In all these infusion systems, the rotor rotation of the dispensing device, which consequently operates the medication dispensing pump, is controlled directly, preferably by magnetic coupling to the control device, which in turn contains a rotor which, during the infusion step, rotates integrally with the rotor of the dispensing device. In certain embodiments, there may be an electromagnetic coupling between actuating rotor and actuated rotor, in which the latter takes the form of a stator.

However, it has been noted by the Applicant that the patient is not always able to keep the control device in a steady position near the dispensing device during the whole infusion step, which normally lasts 5-15 seconds, but it may happen that the control device is accidentally rotated clockwise or counter-clockwise when coupled. This accidental rotation modifies the coupling between the control device and the dispensing device so that, if the accidental rotation of the control device occurs in the same direction of rotation of the rotor of the dispensing device, there will be an over-rotation and therefore the dispensing of a dose greater than desired while, if the accidental rotation occurs in the opposite direction, there will be an under-dosage of the medication.

SUMMARY OF THE INVENTION

It is an object of the present invention to provide an infusion system of the type described above, but which can avoid the aforesaid drawback of over-dosage or under-dosage of the medication in case of accidental rotation of the control device by of the patient.

This and other objects are achieved by an infusion system as outlined in the appended claims, the definitions of which form an integral part of the present description.

Further features and advantages of the present invention will become apparent from the description of some preferred embodiments thereof, given hereinafter by way of a non-limiting example only.

DETAILED DESCRIPTION OF THE INVENTION

Figure 1:
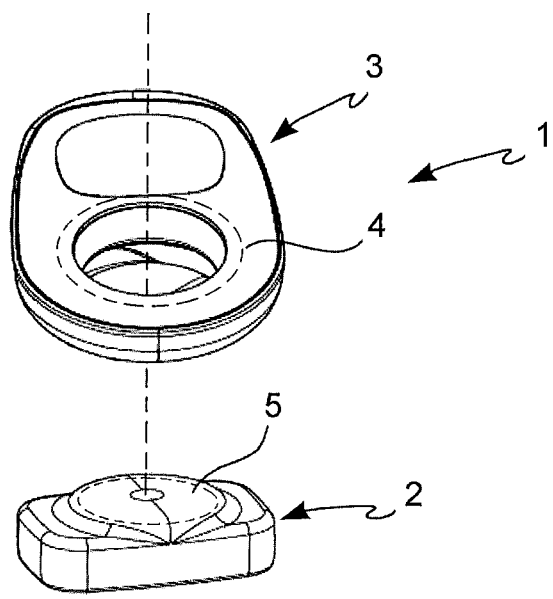
FIG. 1 shows a perspective view of the infusion system of the invention in a non-operating condition.

The present invention relates to an infusion system, preferably trans-dermal infusion, of a medication to a patient.

The term "trans-dermal infusion" as used in the present disclosure indicates that the medical device is adapted to administer trans-dermally, i.e. through the skin, a medication to a patient by means of one or more needles or other device with direct fluidic exchange with the patient's body. The term "trans-dermal infusion" also includes intra-muscular, intra-venous or similar administration, provided that such administration provides for penetration of the patient's skin.

In certain embodiments, the dispensing device of the system according to the invention can be implanted under the skin.

The term "infusion system" refers to an integrated set of medical devices which, when operationally coupled, allow the administration by infusion of a medication to a patient. The infusion system according to the invention may comprise two or more medical devices and may be adapted to administer the medication continuously or semi-continuously for a certain period of time.

The infusion system according to the invention comprises a dispensing device and a control device, as for example described in EP 3138592 A1.

In brief, the dispensing device comprises:
injection means, such as a needle, a catheter or other dispensing means of a medication dose, operable by trans-dermal or subcutaneous route,
a tank for the medication solution for the infusion,
pumping means making the tank fluidly communicating with the injecting means,
a first rotor, or actuated rotor, operationally coupled to the pumping means, for example by means of a mechanical transmission system.

In brief, the control device comprises:
a second rotor, or actuating rotor, operationally coupled, in particular by means of a magnetic coupling, to the first rotor associated with the dispensing device,
means for actuating the second rotor operable according to a predefined protocol for administering the medication.

The tank for the medication solution is typically adapted to contain a plurality of doses to be administered. For example, daily doses, or doses for two or more days, typically up to a week may be contained in the tank.

In certain embodiments, the tank is removable from the dispensing device and is of the disposable type, so that it can be replaced by another preloaded tank.

In other embodiments, the tank is attached to the medication dispensing device and is rechargeable, by means of an appropriate loading valve or by a pierceable septum.

In yet other embodiments, the tank is attached to the medication dispensing device and the entire dispensing device is of the disposable type, or the dispensing device is disposable with the exception of the injection means that can remain inserted in the patient's body, at least for a certain period of time dictated by normal medical practice.

The tank may be made of a rigid or flexible material, suitable for medical use.

The pumping means may be of any kind.

In certain embodiments, the pumping means are an axial pump, for example a piston pump. A typical example is a syringe for injections.

In other embodiments, the pumping means are a peristaltic pump, a membrane pump, a micropump with rotary and vibrating elements or similar devices known in the art.

The pumping means may be connected directly or comprise the medication tank (as in the case of a syringe type piston pump), or be connected to the tank and/or to the injection by means of a conduit. The conduit, upstream and/or downstream of the pumping means, may be intercepted by a valve, for example a check valve or a closing valve or
a valve that is air-permeable but not permeable to the medication.

The rotor is coupled to the pumping means by a suitable motion transmission member. This coupling may be of any type, e.g. mechanical, magnetic, electro-magnetic, but preferably it is a mechanical coupling. In certain embodiments, the rotor is mechanically coupled to the pumping means in a direct manner, for example by means of a transmission shaft, as for example it can occur when the pumping means are a peristaltic pump. However, in preferred embodiments, the rotor is coupled to the pumping means by a gear transmission member, for example by means of a reduction system.

In certain embodiments, the first rotor, i.e. the actuated rotor of the dispensing device, comprises rotation stop means, which can be deactivated by interaction with the control device, when the latter is operationally coupled to the dispensing device. In a preferred embodiment, described for example in patent application EP 3138594 A1, the stop means consist of a series of tabs movable, by magnetic attraction, between a lowered position—in which the tabs engage in complementary seats arranged inside the dispensing device—and a raised unlock position.

In certain embodiments, the dispensing device further comprises an irreversible locking unit for the rotation of the rotor or for the actuation of the pumping means, which can be automatically activated in case of malfunction of the dispensing device (e.g., due to obstruction of the injection means and/or pumping means and/or conduits or due to damage or malfunction of the mechanical parts of the device; or again if the tank is empty). Such a locking unit may be made in various manners and is widely described in patent application EP 3138592 A1, the description of which is fully referred to in the present patent application.

The control device, as mentioned, comprises a second rotor, i.e. an actuating rotor operationally coupled to the first rotor present in the dispensing device. In preferred embodiments, the coupling between the first and second rotors takes place by electro-magnetic means or, more preferably, by magnetic coupling. Thereby, an operative proximity coupling is obtained, i.e. without the need for a physical contact between the dispensing device and the control device. In fact, the dispensing device may be placed under a patient's garment, whereby the control device can transfer the dispensing energy to the dispensing device through the garment, generally by contact with the surface of the garment itself. In the event that the dispensing device is positioned on a part of the body easily accessible by the same patient, it will also be possible to have a direct contact between the control device and the dispensing device, without this affecting or otherwise modifying the operation of the system.

In certain embodiments, the operative proximity coupling between the first and second rotors is accomplished by arranging a series of magnetic elements on one of the two rotors and a corresponding series of ferromagnetic or magnetic elements on the other. Thereby, the rotation of the second rotor positioned on the control device will take place integrally with the rotation of the first rotor when the two devices are operationally coupled. At the same time, if the first rotor comprises the stop means described above, the magnetic attraction with the second rotor will also cause the release of said stop means. Vice versa, when the control device is removed from the coupling to the dispensing device, the stop means of the first rotor can return, for example due to an elastic effect, to the initial stop position.

The control device also comprises means for actuating the second rotor. Such actuation means may be implemented by manual actuation, for example by means of a knob operable manually by the patient for the turn or series of turns necessary for the total dispensing of the required dose, or, more preferably, by a suitable motorization, operable by switch, button or other control system.

The control device will also comprise a command and control unit, as will be better described in the following description, so as to switch the command given by the patient into a programmed administration command of the required medication dose.

The control device may also comprise an automatic system for selecting the dose to be administered.

The infusion system known from the prior art has been briefly described thus far, in particular from the patent applications/patents of the Applicant discussed above and more precisely from patent application EP 2910263 A1, the description of which, as said, is fully referred to in the present description with respect to the known components of the infusion system. For those embodiments in which such components have been modified or integrated, the following description will provide the required details.

Figure 2:
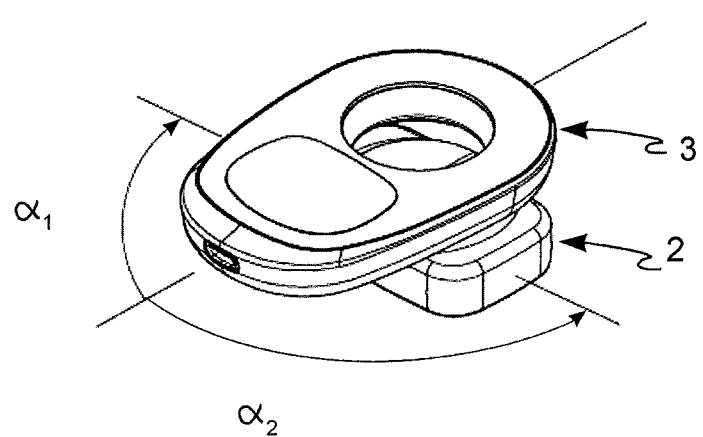
FIG. 2 shows a perspective view of the infusion system of the invention in an operating condition.

In a general embodiment, with reference to the figures, the present invention relates to an infusion system 1 as defined above, comprising a dispensing device 2 of a medication solution and a control device 3 of the operation of the dispensing device 2, wherein the control device 3 comprises an actuating rotor 4 (shown in transparency) with an annular shape and the dispensing device 2 comprises an actuated rotor 5 (shown in transparency) set in rotation by said actuating rotor 4 of the control device 3 and wherein the infusion system 1 can be configured in a non-operating configuration, in which the dispensing device 2 and the control device 3 are spaced apart from each other (FIG. 1), and in an operating configuration, in which the dispensing device 2 and the control device 3 are temporarily proximity-coupled (FIG. 2), and wherein the actuating rotor 4 of the control device 3 and the actuated rotor 5 of the dispensing device 2 are arranged so that they are functionally coupled.

The term "in proximity" or "proximity" means a situation in which the dispensing device 2 and the control device 3 are not in contact, but are positioned at a distance such as to allow the actuated rotor 5 of the dispensing device 2 to be actuated by the actuating rotor 4 of the control device 3, in particular at a distance such as to allow the transfer of magnetic or electromagnetic energy from the actuating rotor 4 to the actuated rotor 5.

The term "functional coupling" between actuating rotor 4 and actuated rotor 5 means a proximity coupling between the two devices such as to allow rotation of the actuated rotor 5 induced by the actuating rotor 4. This coupling can take place even when the axes of the two rotors are not perfectly coincident, but alongside in a condition of parallelism or inclined with respect to each other.

The invention is characterised in that it comprises the means for compensating or blocking the relative rotation of the control device 3 with respect to the dispensing device 2.

In fact, as discussed in the introductory part of the present description, it has been noted by the current inventors that, once the patient has brought the control device 3 in the proximity of the dispensing device 2 applied to his/her body, there is the risk that the initial position of the control device 3 is not maintained, but that it is accidentally rotated in one direction or the other by a certain angle (see FIG. 2, angle α1 clockwise or angle α2 counter-clockwise), which normally will not be greater than ±90°. It should be noted that the initial positioning of the control device 3 in the proximity of the dispensing device 2, i.e. the initial relative angle at which the two devices are located, does not affect the correctness of the infusion operation, since the magnetic interaction between the actuated rotor 5 of the dispensing device 2 and the actuating rotor 4 of the control device 3 occurs almost continuously, i.e. with an irrelevant displacement for the dose, along the circumference of the two rotors. The problem arises instead once the coupling has been made and in particular during the administration that can take place automatically or after the dispensing command has been given and/or the dispensing of the medication (and hence the rotation of the actuating rotor 4) has started since, assuming that the regular rotation of the actuating rotor 4 takes place in a clockwise direction, the angular displacement according to an angle α1 clockwise or angle α2 counter-clockwise of the control device 3 would respectively cause an over- or under-dosage of the medication. Obviously, if the actuating rotor 4 was set to rotate counter-clockwise, the effect would be opposite.

The invention addresses this technical problem by proposing the solution defined above in the statement of the general embodiment and detailed in the following particular embodiments.

Figure 3:
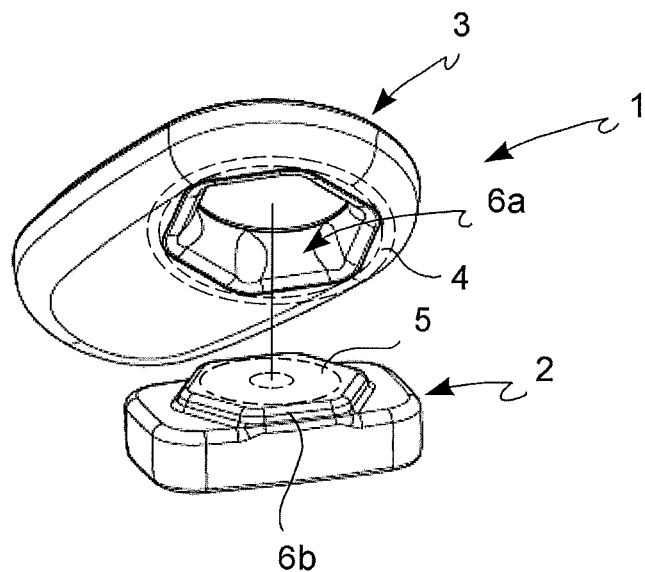
FIG. 3 shows a perspective view of a first embodiment of the infusion system of the invention in a non-operating condition.

FIG. 3 shows a first embodiment of the invention, in which the infusion system 1 comprises means for blocking the relative rotation of the control device 3 with respect to the dispensing device 2.

The blocking means comprise complementary profiles 6a, 6b with a shape coupling of the control device 3 to the dispensing device 2. In the embodiment in FIG. 3, these complementary profiles 6a, 6b comprise:
  a relief 6b with a non-circular shape, specifically hexagonal, arranged on the face of the dispensing device 2, in a coaxial position with the actuated rotor 5, and
  a non-circular seat 6a, specifically hexagonal, complementary to the relief 6b, arranged on the control device 3, in a coaxial position with the actuating rotor 4.

It should be understood that the hexagonal shape of the seat 6a and of the relief 6b is just an example, since any other complementary shape which can avoid the relative rotation of the control device 3 with respect to the dispensing device 2, for example a triangular, square, pentagonal, star, ellipse shape, etc., falls within the scope of the invention.

Thereby, the mutual rotation between control device 3 and dispensing device 2 is prevented.

An advantage of this embodiment is the manufacturing simplicity, however it also has the drawback of requiring a direct contact, or at most through the interposition of a light garment, between control device 3 and dispensing device 2, so as to obtain the shape coupling between the two devices.

In other embodiments, the infusion system 1 comprises means for compensating the relative rotation of the control device 3 with respect to the dispensing device 2. Such compensating means do not prevent the accidental rotary displacement of the control device 3 with respect to the dispensing device 2, but they prevent this accidental displacement from causing a substantial variation in the dose of medication administered to the patient with respect to the programmed dose.

The compensation means may be mechanical or electronic.

In certain embodiments, the compensating means are of the mechanical type. The term "mechanical compensation means" means both transmission means, for example gears, with a given transmission ratio, and means for fluidic adjustment between the medication tank and the injection means, for example by means of an appropriate sizing of the fluidic conduits.

In such embodiments, of which those shown in FIGS. 4A-4B and 5A-5B are particular but not exhaustive examples, the means for compensating the relative rotation of the control device 3 with respect to the dispensing device 2 are implemented by means of transmission members 7, 107 of the motion from the actuated rotor 5 to the pumping means 8 of the medication solution, sized so that any positive or negative difference in the rotation of the actuated rotor 5, with respect to a programmed rotation, up to ±90°, will correspond to a positive or negative difference in the administered dose, which will be 10% lower or equal by volume, or 5% lower or equal by volume, or 3% lower by volume, even more preferably 1% lower by volume than the programmed dose.

The term "positive or negative rotation difference" means the difference in rotation induced by the accidental rotation by an angle α1 or α2 of the control device 3 with respect to the dispensing DEVICE 2, respectively in the same direction or in the opposite direction of the programmed rotation caused by the interaction of the actuating rotor 4 of the control device 3 with the actuated rotor 5.

The term "programmed rotation" means the rotation of the actuating rotor 4 of the control device 3 necessary for administering a programmed dose of the medication product to the patient.

The term "programmed dose" refers to a single dose of a medication product that, depending on the therapy, must be administered to a patient through the infusion system of the invention.

More precisely, the transmission members 7, 107 have a high transmission ratio, preferably greater than or equal to 7.

Figure 4A:
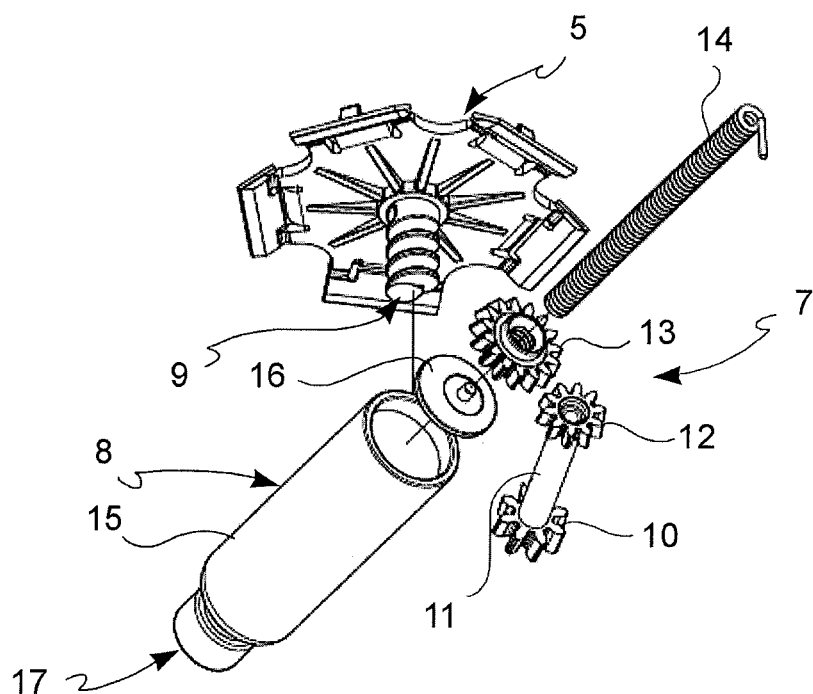
FIG. 4A shows a perspective bottom exploded view of a detail of the mechanism for transmitting motion between the rotor and the pump in the dispensing device in an embodiment of the invention.
Figure 4B:
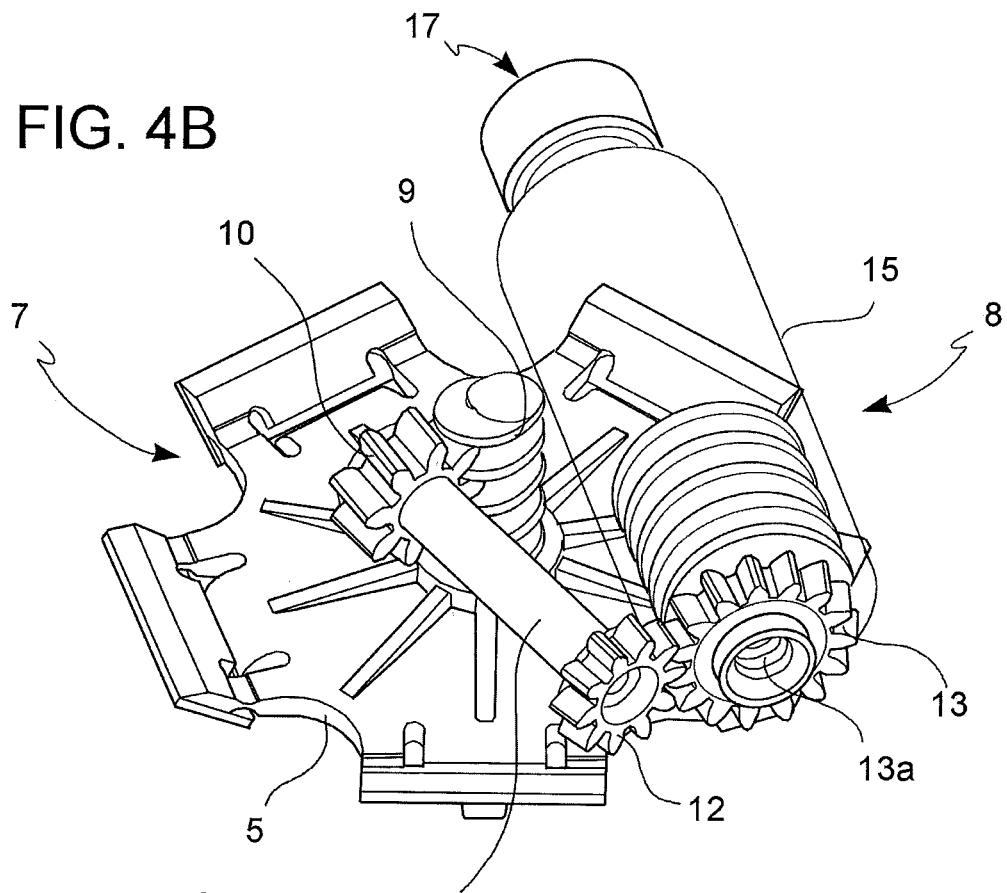
FIG. 4B shows a different perspective bottom view of the detail in FIG. 4A in an assembled condition.

FIGS. 4A-4B show a first embodiment of the transmission members 7.

The figures show an actuated rotor 5 comprising, on the face facing downwards, a threaded cylinder 9. The threaded cylinder 9 meshes with a first gear wheel 10. The gear wheel 10 is integral with a shaft 11, to which a second gear wheel 12 is integral, wherein preferably the second gear wheel 12 has a greater number of gears than the first gear wheel 10.

The second gear wheel 12 meshes on a third gear wheel 13, or driven gear wheel, which comprises a threaded coaxial hole 13a, which threaded hole 13a is operationally associated with a threaded piston 14. The threaded piston 14 is preferably made by means of a helical spring, so as to be flexible, adapting itself to the reduced space requirements of the casing of the dispensing device 2.

The threaded piston 14 may be inserted into a hollow cylinder 15 and comprises a plate 16 at the end of the threaded piston 14 inside the cylinder 15. The cylinder 15 is the tank for the medication solution, while the piston 14, plate 16 and cylinder 15 assembly is the pumping means 8 of the dispensing device 2, in particular an axial piston pump.

The cylinder 15 comprises a dispensing hole 17 at the opposite end to that in which the threaded piston 14 is inserted. The injection means (not shown) as defined above are normally associated with the dispensing hole 17.

In operation, the rotation of the actuated rotor 5 causes the rotation of the shaft 11 and therefore of the driven gear wheel 13. Since this is fixed, its rotation causes the advance (or in the case of reverse rotation, the retraction) inside the cylinder 15 of the threaded piston 14 inserted in the driven gear wheel 13 and therefore its medication pumping and dosing action.

The gear transmission ratio is given by the product of the transmission ratio of the threaded cylinder 9/first gear wheel 10 with the transmission ratio of the second gear wheel 12/driven gear wheel 13 and is preferably greater than 10, more preferably greater than or equal to 12.

By operating at this gear transmission ratio and appropriately sizing the threads of the inner hole 13a of the driven gear wheel 13 and of the threaded piston 14 and the inner diameter of the hollow cylinder 15, the dose difference administered below the limits previously indicated can be obtained.

This sizing of the transmission members 7 is per se conventional and easily achievable by a mechanical designer skilled in the art.

Figure 5A:
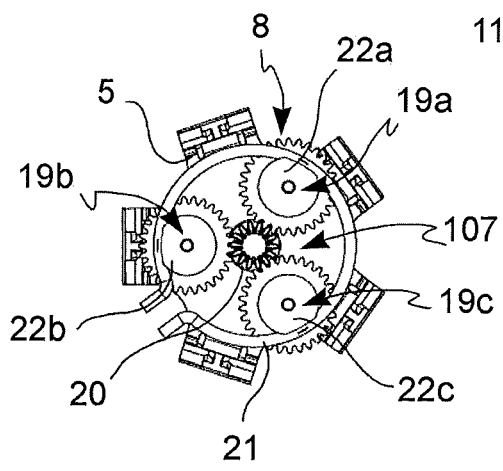
FIG. 5A shows a plan bottom view of a detail of the mechanism for transmitting motion between the rotor and the pump in the dispensing device in a further embodiment of the invention.
Figure 5B:
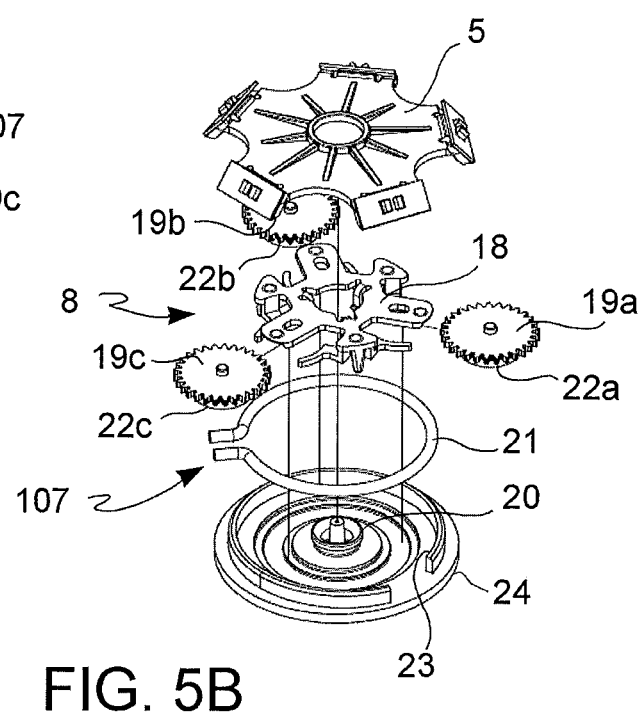
FIG. 5B shows an exploded view of the detail in FIG. 5A.

FIGS. 5A-5B show a different embodiment of the transmission means 107. The figure shows pumping means 8 consisting of a peristaltic pump of the type described in patent application EP 2910263 A1 by the same Applicant, to which reference should be made for a complete description.

Briefly, the figures show an actuated rotor 5 coaxially associated with a support plate 18. Along the periphery of the support plate 18, three gear wheels 19a, 19b, 19c are idly hinged. The three gear wheels 19a, 19b, 19c mesh with a gear wheel 20, placed in a coaxial position with respect to the axis of the actuated rotor 5, thus making up an epicyclic gear system with planetary movement. In practice, the rotation of the actuated rotor 5 causes the support plate 18 to rotate through the gears. Consequently, the three gear wheels 19a, 19b, 19c perform a revolution movement around the axis of the actuated rotor 5 and at the same time, due to the meshing with the central gear wheel 20, also rotate about their own axis.

The three gear wheels 19a, 19b, 19c further comprise a circular relief 22a, 22b, 22c which presses against a flexible pipe 21. The pipe 21 is in flow communication on one side with a tank of the medicament solution (not shown) and on the other side with the medicament dose injection means (not shown). The section of the pipe 21 on which the circular reliefs 22a, 22b, 22c of the three gear wheels 19a, 19b, 19c exert pressure is arranged as a ring in a seat 23 placed on a base plate 24.

In operation, the revolution movement and simultaneous rotation about their own axis of the three gear wheels 19a, 19b, 19c causes a pumping action of the peristaltic type on the pipe 21.

By suitably sizing the diameter of the three gear wheels 19a, 19b, 19c and the inner diameter of the pipe 21, the difference in dose administered below the previously indicated limits can be obtained.

This sizing of the transmission members 107 is per se conventional and easily achievable by a mechanical designer skilled in the art.

The embodiments described above, in which the compensation means are of the mechanical type, are per se of easy design but require a high degree of accuracy in their construction which can affect the cost thereof.

In different embodiments, the compensating means are of the electronic type.

In certain embodiments, the compensating means are implemented by integrating in the dispensing device 2 a rotation sensor and a transponder adapted to communicate wirelessly with the control device. The term "wirelessly" means, for example, a WiFi, Bluetooth, NFC (Near Field Communication) communication or any other communication system that does not require a physical connection between the two devices. The transponder may be for example an RFID device, an NFC or a device as described in EP 2 764 881 by the same Applicant.

The rotation sensor is configured to detect the rotation angle $\beta$ of the actuated rotor 5 relative to a reference angle. The rotation sensor may be, for example, an optoelectronic sensor or a Hall-effect, inductive, capacitive rotation sensor, etc.

The rotation sensor can communicate with the control device 3 continuously or intermittently.

In certain embodiments, the transponder communicates continuously with the control device 3.

Figure 6:
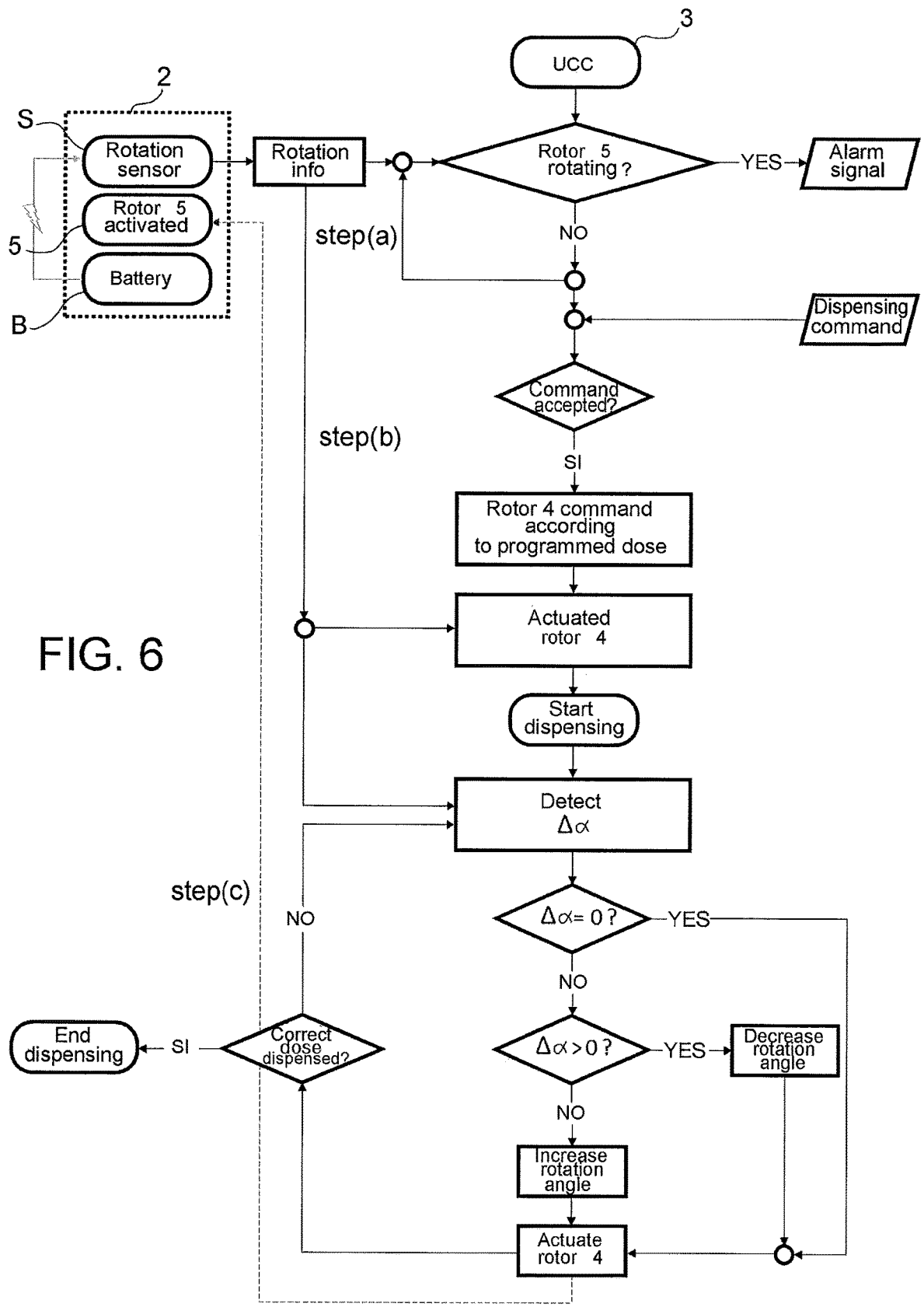
FIG. 6 shows a block diagram of a first embodiment of a compensation system of the rotor rotation with electronic control.

In such embodiments, shown by the block diagram in FIG. 6, the dispensing device 2 comprises a rotation sensor S communicating via a transponder with the control device 3 and a power source B, for example a battery or a rechargeable battery or a condenser, to supply the rotation sensor S and the transponder. The rotation sensor S detects continuously and the transponder communicates continuously to the control device 3, when the latter is in the wireless communication range of the transponder, the data relative to the rotation of the rotor 5. By the term "continuously" it is meant a rotation detection and a communication at limited time intervals (in the interval of 1 millisec-1 sec) and without interruptions.

The control device 3 instead comprises a command and control unit (UCC) which receives the rotational information of the rotation sensor S and processes it so as to modify, if necessary, the rotation angle of the actuating rotor 4 and therefore compensate for the positive or negative differences in the rotation angle $\beta$ of the actuated rotor 5 caused by an accidental rotary movement according to an angle $\alpha 1$ or $\alpha 2$ of the control device 3 by the user, when the system of the invention is in an operating condition.

By the term "command and control unit" or "UCC" it is meant a system consisting of one or more microprocessors and optionally of other devices adapted to receive, send or detect signals and/or commands and/or to communicate between the various devices of the UCC and with sensors, actuation means or other external devices.

As shown in FIG. 6, the rotation sensor S of the dispensing device 2 sends rotational information to the UCC of the control device 3, so as to determine whether, for some reason, the actuated rotor 5 is accidentally rotating and, in the affirmative case, it sends an alarm signal (step (a)).

Vice versa, in the case of normal operation, the patient, after having selected the dose on the control device 3, places it in proximity of the dispensing device as described above, sends a dispensing command to the system 1, either acting by pushbutton, switch or similar control means on the dispensing device 3 or automatically, as soon as the system becomes aware of being in the dispensing position.

The UCC of the latter then starts the procedure for dispensing a programmed dose of the medication (step (b)).

During dispensing (step (c)), the UCC constantly monitors the deviation of the effective rotation angle $\beta$ of the actuated rotor 5 with respect to the rotation angle imposed by the actuator rotor 4 ($\Delta\beta$): if $\Delta\beta=0$, the dispensing procedure proceeds regularly and the actuating rotor 4 continues its rotation as programmed; if instead $\Delta\beta>0$, the UCC reduces the rotation angle of the actuating rotor 4 with respect to the angle corresponding to the programmed dose by a value corresponding to $\Delta\beta$ detected, thus compensating for this variation; if instead $\Delta\beta<0$, the UCC increases the angle of rotation by a value corresponding to the $\Delta\beta$ detected, compensating also in this case for this variation. Upon reaching the correct dispensed dose (i.e. when the rotation of the actuating rotor 4 has travelled the programmed angle, possibly compensated as described above), the dispensing is interrupted and the patient can remove the control device 3 from the proximity condition with the dispensing device 2. For example, an audible or luminous or vibrating signal can warn the patient of the end of dispensing.

The term "programmed angle" means the predefined rotation angle necessary for the dispensing of a programmed dose of the medication product. This angle will generally be greater than 360°, preferably greater than 720°, more preferably greater than 1080°, which means that the actuated rotor 5 will have to perform various complete rotations to dispense a dose of the medication product. The dispensing step therefore lasts 3 to 20 seconds, typically about 10 seconds.

In summary, in this embodiment the invention relates to an infusion system 1 of the invention, comprising a dispensing device 2, which comprises a rotation sensor S and a transponder for sending data detected by the rotation sensor S, and a control device 3, which comprises a command and control unit (UCC), wherein said UCC is configured so as to:

send a dispensing command to actuate the actuating rotor 4 of the control device 3;

receive the data concerning the rotation angle $\beta$ of the actuated rotor 5 detected by the rotation sensor S;

calculate the difference $\Delta\beta$ of said rotation angle $\beta$ with respect to the programmed rotation angle;

if $\Delta\beta>0$, send a command for the actuating rotor 4 of the control device 3 in order to decrease the rotation angle by a value corresponding to the calculated $\Delta\beta$;

if $\Delta\beta<0$, send a command for the actuating rotor 4 of the control device 3 in order to increase the rotation angle by a value corresponding to the calculated $\Delta\beta$;

send an end-of-dispensing command to the actuating rotor 4 of the control device 3 when the actuated rotor 5 has completed the programmed rotation angle.

The expression "send a command to the actuating rotor" means sending to the actuating means of the actuation rotor 4 a command (for example, starting, stopping, accelerating, delaying, switching on, switching off, etc.) directly or indirectly.

The embodiment described above is particularly indicated if the dispensing device 2 does not comprise means for blocking the rotation of the actuated rotor 5 of the type described above. In the absence of such means, in fact, the actuated rotor 5 may perform undesired rotations even when the control device 3 is remote and therefore when the system is in non-operating conditions.

In a different embodiment, for example when the dispensing device 2 comprises said stop means for the rotation of the actuated rotor 5, the rotation sensor S operates in a discontinuous manner, as it is activated only when the control device 3 is in proximity of the dispensing device 2 or when the patient has sent a command to dispense the programmed dose of medication.

Figure 7:
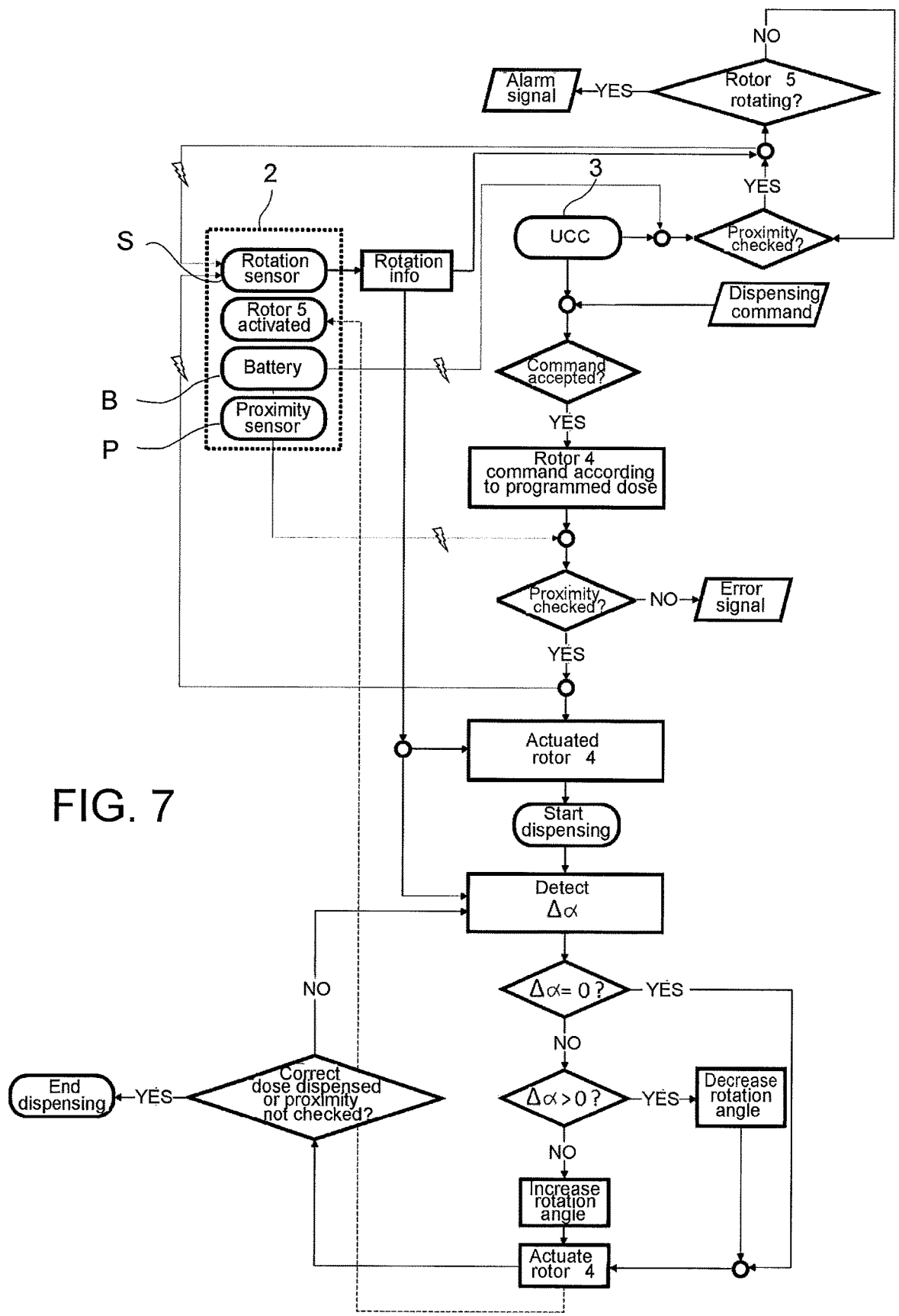
FIG. 7 shows a block diagram of a second embodiment of a compensation system of the rotor rotation with electronic control.

In this embodiment shown in the block diagram in FIG. 7, the invention relates to an infusion system 1 of the invention, comprising a dispensing device 2, which comprises a rotation sensor S and a transponder for sending data detected by the rotation sensor S, and a control device 3, which comprises a command and control unit (UCC), wherein the dispensing device 2 further comprises a proximity sensor P configured to detect, via the transponder, the proximity of the control device 3 and activate the rotation sensor S, and wherein said UCC is configured so as to:

send a dispensing command to the actuating rotor 4 of the control device 3;
receive the data concerning the rotation angle β of the actuated rotor 5 detected by the rotation sensor S;
calculate the difference Δβ of said rotation angle β with respect to the programmed rotation angle;
if Δβ>0, send a command for the actuating rotor 4 of the control device 3 in order to decrease the rotation angle by a value corresponding to the calculated Δβ;
if Δβ<0, send a command for the actuating rotor 4 of the control device 3 in order to increase the rotation angle by a value corresponding to the calculated Δβ;
send an end-of-dispensing command to the actuating rotor 4 of the control device 3 when the actuated rotor 5 has completed the programmed rotation angle.

In a variant of the aforesaid embodiment, the proximity sensor P is positioned on the control device 3 instead of the dispensing device 2 and is configured so as to send, via the transponder, a trigger signal to the rotation sensor S of the dispensing device 2.

The term "trigger signal" or "trigger command" means a signal or command that causes the activation of the sensor and/or its ability to operate on the basis of its function and/or its ability to send data relating to its sensor function.

In a different variant of the above embodiment, the dispensing device 2 does not comprise an energy source, but is energized by induction from the control device 3 when the latter is in a condition of proximity with the dispensing device 2. In this embodiment, the proximity sensor P may also be omitted, since the rotation sensor S is activated only when the control device 3 is in the proximity condition with the dispensing device 2.

Figure 8:
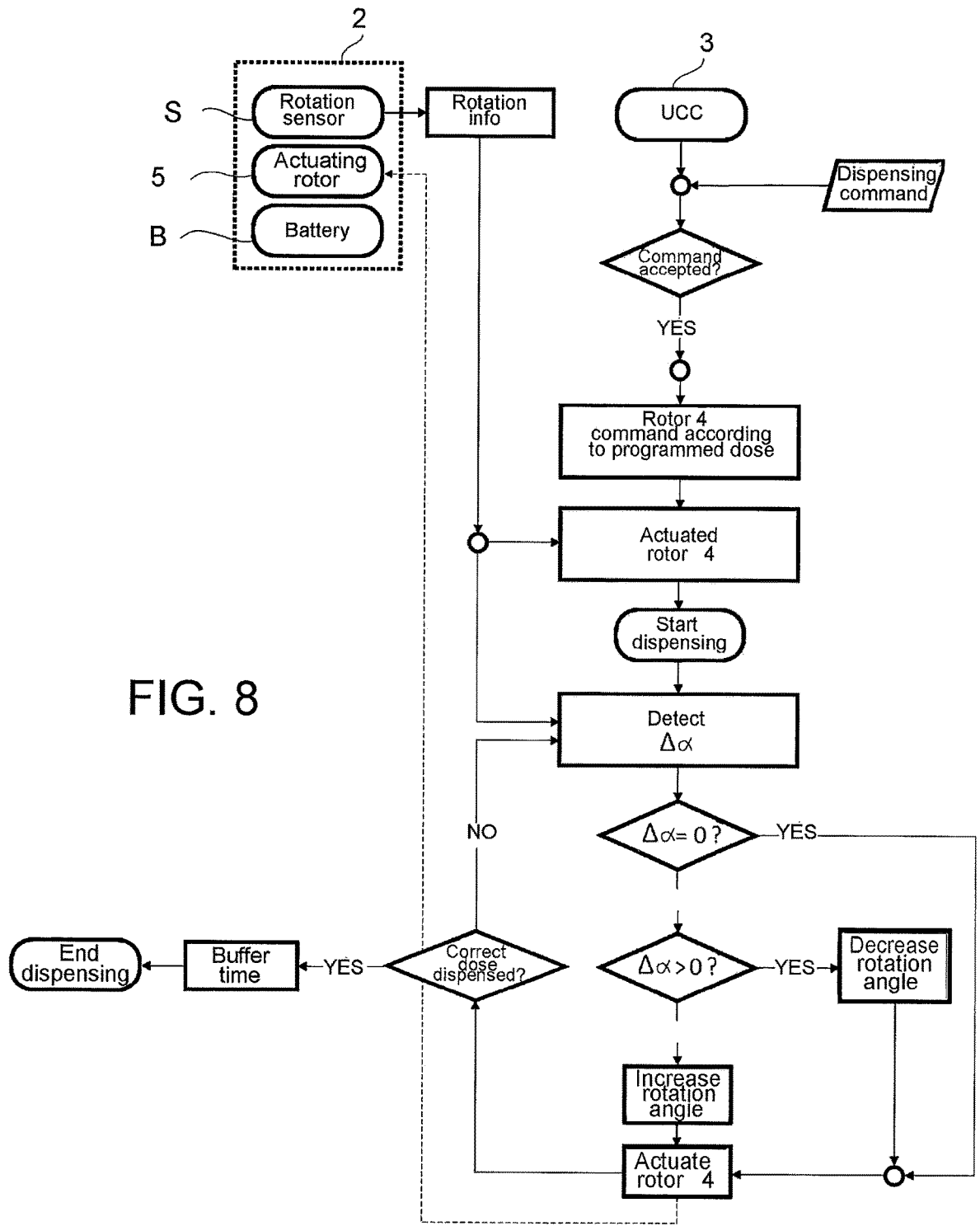
FIG. 8 shows a block diagram of a third embodiment of a compensation system of the rotor rotation with electronic control.

In a further embodiment shown in the block diagram in FIG. 8, the invention relates to an infusion system 1 of the invention, comprising a dispensing device 2, which comprises a rotation sensor S and a transponder for sending data detected by the rotation sensor S, and a control device 3, which comprises a command and control unit (UCC), wherein said UCC is configured so as to:

send a trigger command to the rotation sensor S following a command for the dispensing of a programmed dose of medication by a user;
send a dispensing command to the actuating rotor 4 of the control device 3;
receive the data concerning the rotation angle β of the actuated rotor 5 detected by the rotation sensor S;
calculate the difference Δβ of said rotation angle β with respect to the programmed rotation angle;
if Δβ>0, send a command for the actuating rotor 4 of the control device 3 in order to decrease the rotation angle by a value corresponding to the calculated Δβ;
if Δβ<0, send a command for the actuating rotor 4 of the control device 3 in order to increase the rotation angle by a value corresponding to the calculated Δβ;
send an end-of-dispensing command to the actuating rotor 4 of the control device 3 when the actuated rotor 5 has completed the programmed rotation angle.

The embodiments described above have the drawback of requiring electronic components on the dispensing device 2. Considering that this device is preferably of a disposable type, this solution, although effective from the functional point of view, increases the costs of the infusion system of the invention.

Therefore, in certain embodiments, the electronic components are present only on the control device 3. In these embodiments, the system 1 comprises a control device 3 comprising:

an actuating rotor 4,
a command and control unit (UCC),
a sensor for detecting the movement of the control device 3, for example a gyroscopic device, configured so as to detect a rotary movement of an angle α1, α2 of the control device 3 around the rotation axis of the actuating rotor 4,
optionally, a proximity sensor configured to detect the proximity condition of the control device 3 with respect to the dispensing device 2,
wherein the UCC is configured so as to:
a) optionally, receive a proximity signal to the dispensing device 2 by the proximity sensor;
b) send an activation signal for the motion sensor;
c) send a dispensing command to the actuating rotor 4 of the control device 3;
d) receive data concerning an angle α1, α2 and a rotation direction of the control device 3 detected by the motion sensor;
e) calculate the difference of said rotation angle α1, α2 of the control device 3 with respect to the start-of-detection position;
f) if the calculated difference in the rotation angle α1, α2 of the control device 3 is in the rotation direction of the actuating rotor 4, send a command for the actuating rotor 4 of the control device 3 in order to reduce the rotation angle of the actuating rotor 4 by a value corresponding to such calculated difference, thus obtaining a recalculated rotation angle of the actuating rotor 4;
g) if the calculated difference in the rotation angle α1, α2 of the control device 3 is in the direction opposite to the rotation of the actuating rotor 4, send a command for the actuating rotor 4 of the control device 3 in order to increase the rotation angle of the actuating rotor 4 by a value corresponding to such calculated difference, thus obtaining a recalculated rotation angle of the actuating rotor 4;
h) send an end-of-dispensing command for the actuating rotor 4 of the control device 3 when the actuating rotor 4 has completed the recalculated rotation angle.

In a variant of the above embodiment, the control device 3 further comprises a rotation sensor, for example a Hall-effect sensor, for detecting the actual rotation of the actuated rotor 5 of the dispensing device 2. In this case, the UCC of the control device 3 is configured to:
a) optionally, receive a proximity signal to the dispensing device 2 by the proximity sensor;
b) send an activation signal for the motion sensor;
c) send a dispensing command to the actuating rotor 4 of the control device 3;
d) receive data concerning an angle α1, α2 and a rotation direction of the control device 3 detected by the motion sensor;

e) calculate the difference of said rotation angle α1, α2 of the control device 3 with respect to the start-of-detection position;

f) if the calculated difference in the rotation angle α1, α2 of the control device 3 is in the rotation direction of the actuating rotor 4, send a command for the actuating rotor 4 of the control device 3 in order to reduce the rotation angle of the actuating rotor 4 by a value corresponding to such calculated difference, thus obtaining a recalculated rotation angle of the actuating rotor 4;

g) if the calculated difference in the rotation angle α1, α2 of the control device 3 is in the direction opposite to the rotation of the actuating rotor 4, send a command for the actuating rotor 4 of the control device 3 in order to increase the rotation angle of the actuating rotor 4 by a value corresponding to such calculated difference, thus obtaining a recalculated rotation angle of the actuating rotor 4;

g1) detect the rotation angle β travelled by the actuated rotor 5 of the dispensing device 2;

g2) determine the possible variation Δβ;

g3) send a rotation correction command to the actuation rotor 4;

h) send an end-of-dispensing command for the actuating rotor 4 of the control device 3 when the actuating rotor 4 has completed the recalculated or corrected rotation angle.

It is apparent that only some particular embodiments of the present invention have been described, and those skilled in the art will be able to make all the necessary modifications for the adaptation thereof to particular applications, or combine two or more embodiments, without departing from the scope of protection of the present invention.

What we claim is:

1. An infusion system for infusing a medication in a patient, comprising a medication dose dispensing device and a control device for controlling the dispensing device, wherein the dispensing device comprises:
    means for injecting medication in the patient,
    a tank for the medication for the infusion,
    pumping means making the tank fluidly communicating with the injecting means,
    an actuated rotor, operationally coupled with the pumping means,
and wherein the control device comprises:
    an actuating rotor, which can be operationally coupled with the actuated rotor of the dispensing device,
    means for actuating the actuating rotor which can be operated according to a predefined medication administration protocol for administering a programmed dose,
        and wherein the infusion system can be configured in a non-operating configuration, in which the dispensing device and the control device are spaced apart from each other, and in an operating configuration, in which the dispensing device and the control device are temporarily proximity-coupled, and wherein the actuating rotor of the control device and the actuated rotor of the dispensing device are arranged so that they are functionally coupled,
        and wherein the system comprises means for compensating for the relative rotation of the control device with respect to the dispensing device, wherein said means for compensating are of the electronic type.

2. The infusion system according to claim 1, wherein the pumping means are selected from among piston pumps, peristaltic pumps, diaphragm pumps and micro pumps with rotary and/or vibrating elements.

3. The infusion system according to claim 1, wherein:
    the dispensing device comprises a rotation sensor, a transponder adapted to communicate in a wireless mode with the control device, wherein said rotation sensor is configured for detecting, either continuously or non-continuously, a rotation angle β of the actuated rotor with respect to a reference angle and for generating rotational information,
    the control device comprises a command and control unit, configured for receiving the rotational information of the rotation sensor, processing it so as to modify, where necessary, the rotation angle of the actuating rotor and therefore compensate for the positive or negative differences in the rotation angle β of the actuated rotor caused by an accidental rotary movement of the control device by the user.

4. The infusion system according to claim 3, wherein the dispensing device comprises a power supply source.

5. The infusion system according to claim 3, wherein the dispensing device comprises an induction power supply source originating from the control device when the latter is in proximity of the dispensing device.

6. The infusion system according to claim 3, wherein the control device comprises a proximity sensor configured for sending a signal, through the transponder, for activating the rotation sensor of the dispensing device.

7. The infusion system according to claim 3, wherein the dispensing device comprises a proximity sensor configured to detect the proximity of the control device for activating the rotation sensor.

8. The infusion system according to claim 3, wherein said command and control unit is configured to:
    send a dispensing command to actuate the actuating rotor of the control device;
    receive the data concerning the rotation angle β of the actuated rotor detected by the rotation sensor;
    calculate the difference Δβ of said rotation angle β with respect to a programmed rotation angle;
    if Δβ>0, send a command for the actuating rotor of the control device in order to reduce the rotation angle by a value corresponding to the calculated Δβ;
    if Δβ<0, send a command for the actuating rotor of the control device in order to increase the rotation angle by a value corresponding to the calculated Δβ;
    send an end-of-dispensing command for the actuating rotor of the control device when the actuated rotor has completed the programmed rotation angle.

9. The infusion system according to claim 1, wherein the control device comprises:
    a command and control unit,
    a sensor for detecting the movement of the control device configured so as to detect a rotary movement of an angle α1, α2 of the control device around the rotation axis of the actuating rotor.

10. The infusion system according to claim 9, wherein the command and control unit is configured so as to:
    a) actuate the actuating rotor of the control device;
    b) receive data concerning angle α1, α2 and a rotation direction of the control device detected by the movement sensor;
    c) calculate a difference of said rotation angle α1, α2 of the control device with respect to a start-of-detection position;
    d) if the calculated difference in the rotation angle α1, α2 of the control device is in the rotation direction of the actuating rotor, send a command for the actuating rotor of the control device in order to reduce the rotation angle of the actuating rotor by a value corresponding to such calculated difference, thus obtaining a recalculated rotation angle of the actuating rotor;
e) if the calculated difference in the rotation angle $\alpha 1$, $\alpha 2$ of the control device is in the direction opposite to the rotation of the actuating rotor, send a command for the actuating rotor of the control device in order to increase the rotation angle of the actuating rotor by a value corresponding to such calculated difference, thus obtaining a recalculated rotation angle of the actuating rotor;
f) send an end-of-dispensing command for the actuating rotor of the control device when the actuating rotor has completed the recalculated rotation angle.

11. The infusion system according to claim 9, wherein the command and control unit is configured so as to:
a) actuate the actuating rotor of the control device;
b) receive data concerning angle $\alpha 1$, $\alpha 2$ and a rotation direction of the control device detected by the movement sensor;
c) calculate a difference of such rotation angle $\alpha 1$, $\alpha 2$ of the control device with respect to a start-of-detection position; send a command for the actuating rotor in order to compensate for the rotation direction $\alpha 1$, $\alpha 2$.

12. The infusion system according to claim 9, wherein the control device further comprises a rotation sensor for detecting the rotation of the actuated rotor of the dispensing device.

13. The infusion system according to claim 9, wherein the sensor for detecting the movement of the control device is a gyroscopic device.

14. The infusion system according to claim 1, wherein the actuating rotor and the actuated rotor are operationally coupled by means of magnetic coupling.

15. The infusion system according to claim 1, wherein the dispensing device is disposable.

* * * * *